United States Patent [19]

Miyazawa

[11] 4,454,542
[45] Jun. 12, 1984

[54] DEFECT DETECTING METHOD AND APPARATUS

[75] Inventor: Takashi Miyazawa, Urayasu, Japan

[73] Assignee: Kirin Beer Kabushiki Kaisha, Tokyo, Japan

[21] Appl. No.: 401,180

[22] Filed: Jul. 23, 1982

[30] Foreign Application Priority Data

Jul. 30, 1981 [JP]   Japan ................................ 56-118607

[51] Int. Cl.³ ............................................. H04N 7/18
[52] U.S. Cl. ................................... 358/106; 209/526;
250/223 B; 356/240; 356/445
[58] Field of Search .................... 358/106; 250/223 B;
356/240, 445; 209/526

[56] References Cited

U.S. PATENT DOCUMENTS

| | | | |
|---|---|---|---|
| 4,213,702 | 7/1980 | Bryant | 250/223 B |
| 4,256,957 | 3/1981 | Ford | 250/223 B |
| 4,284,353 | 8/1981 | Yoshida | 356/240 |
| 4,293,219 | 10/1981 | Ducloux | 356/240 |
| 4,385,233 | 5/1983 | Lovalenti | 209/526 |
| 4,414,566 | 11/1983 | Peyton | 358/106 |

FOREIGN PATENT DOCUMENTS 49-1943218  11/1974  Japan .
51-108881   9/1976   Japan .
53-17779    2/1978   Japan .

Primary Examiner—Howard W. Britton
Attorney, Agent, or Firm—Ladas & Parry

[57] ABSTRACT

In a defect detecting method and apparatus, the image of an object under inspection is formed, the signals of picture elements forming the image is stored, the picture elements signals are accumulated for each of the regions which form parts of the image, the results of the accumulations for regions proximate to each other are compared, and a defect is detected from the result of the comparison.

11 Claims, 13 Drawing Figures

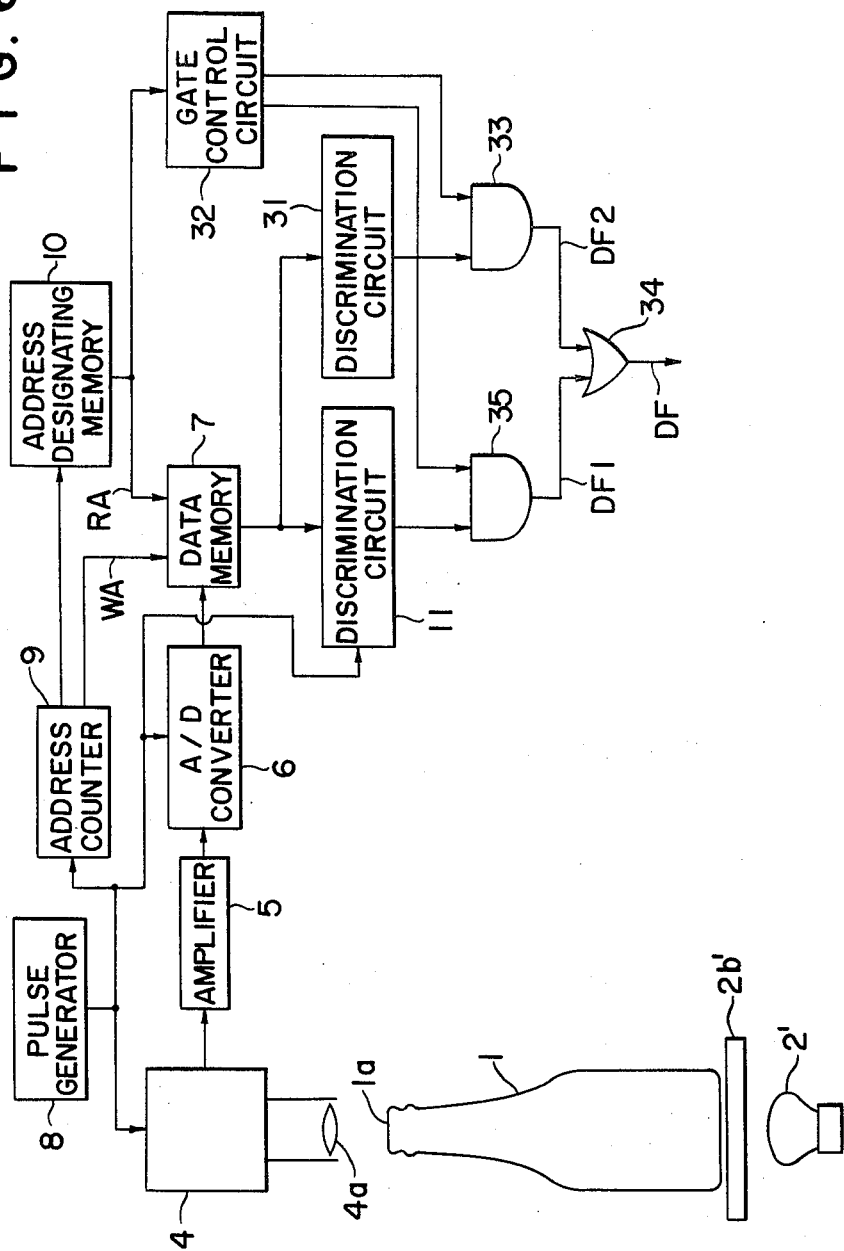

DEFECT DETECTING METHOD AND APPARATUS

BACKGROUND OF THE INVENTION

This invention relates to a method of detecting a defect in an object such as a bottle, and an apparatus for implementing the method.

If a bottle made of glass for wine, alcoholic liquors, soft drinks or foods has a defect such as scratches, cracks or breakages at its mouth, then it is impossible or difficult to completely seal the mouth, and problems in food hygiene occur. Thus, it is necessary to detect a defect and to reject the bottles having a defect. It is also necessary to detect a defect at other parts, such as the bottom of a bottle for maintaining food hygiene.

A variety of methods of detecting defects in bottles have been proposed in the art; however, they still have the following difficulties:

For instance, in a defect detecting apparatus disclosed in Japanese Patent Application Laid-Open No. 108881/1976, a bottle conveyed by a conveyor is stopped at an inspection station, where it is spinned at a high speed, and it is inspected by a pair or plurality of light emitting and light receiving units which are arranged around the mouth of the bottle. However, the apparatus is disadvantageous in that it is intricate in mechanical construction, and its inspection speed is low, e.g., at about one hundred bottles per minute.

Japanese Patent Application Publication No. 43218/1974 and Japanese Patent Application Laid-Open No. 17779/1978 discloses a method in which, while a bottle is passed through an inspection position, light is applied to the mouth portion of the bottle, and light reflected from all the surface of the mouth portion is detected by rotating a prism and a reticle at a high speed, whereby a defect is detected. In this method, it is unnecessary to spin a bottle at a high speed; however, it is necessary to provide a high-speed rotation mechanism for spinning the prism or reticle at a high speed. Accordingly, it is difficult to maintain the accuracy high for a long period of time, and it also difficult to increase the rate of inspection.

Also known in the art is a method in which light reflected from a bottle's mouth portion is detected with a number of light emitting and light receiving units. However, the method has a drawback in that the entire mouth portion cannot be inspected uniformly.

SUMMARY OF THE INVENTION

Accordingly, an object of this invention is to provide a defect detecting method which has improved inspection accuracy and inspection rate, and an apparatus for implementing the method, which is simple in mechanical construction.

The foregoing object and other objects of this invention have been attained by the provision of a defect detecting method and an apparatus for implementing the method, in which light from an object under inspection is received to form the image thereof, the image is divided into a plurality of picture elements, the signals of picture elements are stored in relation to the positions of the corresponding segments or portions of the image, the image is imaginarily divided into a plurality of regions, the picture elements signals thus stored are accumulated for each region; the results of the accumulations for regions proximate to each other are compared to each other; and a defect in the bottle is detected from the result of the comparison.

The nature, principle and utility of the invention will become more apparent for the following detailed description and the appended claims when read in conjunction with the accompanying drawings.

BRIEF DESCRIPTION OF THE DRAWINGS

In the accompanying drawings:

FIG. 6 is a block diagram showing another embodiment of the defect detecting apparatus according to the invention;

DETAILED DESCRIPTION OF THE INVENTION

Figure 1:
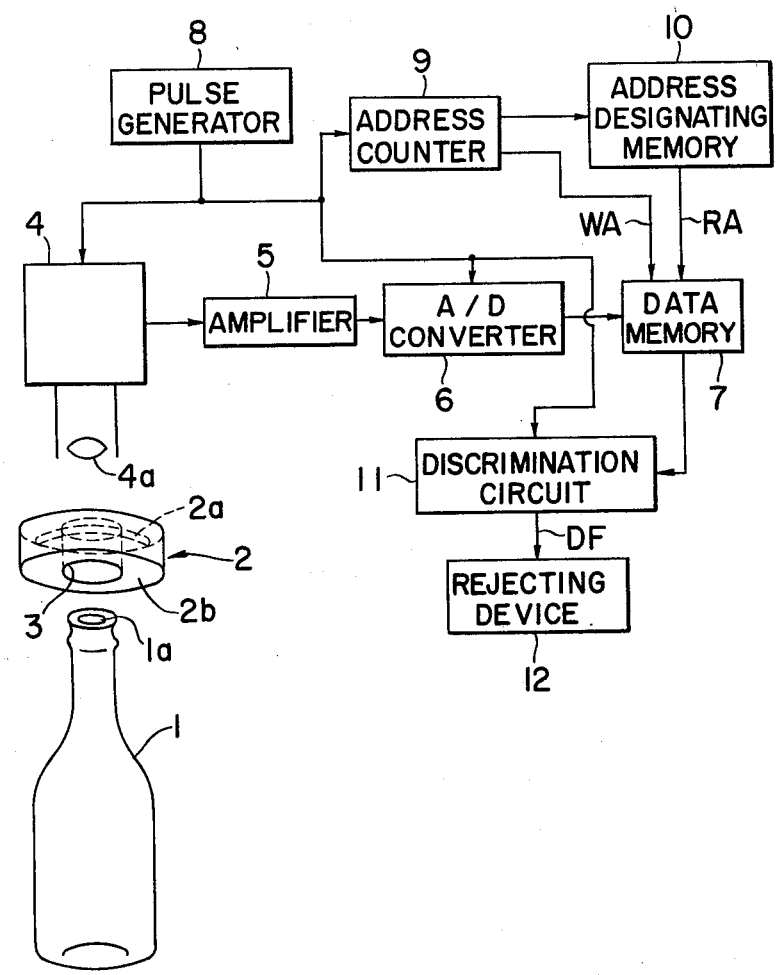
FIG. 1 is a block diagram showing an embodiment of a defect detecting apparatus according to this invention.

An embodiment of a defect detecting apparatus according to this invention is as shown in FIG. 1. The apparatus is to detect defects in the mouth portion of a bottle.

A bottle 1 to be inspected is conveyed by a conveyor (not shown). When the bottle reaches an inspection point or inspection position as shown, its mouth portion 1a is uniformly illuminated by an illuminating device 2, which includes a light source 2a such as an annular fluorescent lamp and a diffusion plate 2b.

The illuminating device 2 is positioned over the bottle 1 at the inspection point. The device 2 has a through-hole 3 at the center, so that light reflected from the bottle's mouth portion advances upwardly through the hole 3. A CCD camera 4 is set over the illuminating device 2, so as to receive the light reflected from the mouth portion, i.e., to allow the image of the mouth portion to be formed through a lens 4a on the CCD light receiving surface. The CCD camera 4 is made up of photoelectric conversion elements which are arranged in 100 lines ×100 columns for instance, thus providing picture element signals corresponding to the brightnesses of a number of minute segments or areas forming the mouth portion of the bottle.

Figure 2:
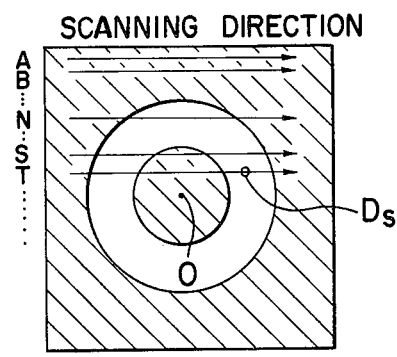
FIG. 2 is an explanatory diagram showing the image of the mouth portion of a bottle.

In general, the optical image of the mouth portion of a bottle is as shown in FIG. 2. In FIG. 2, the part shaded appears relatively dark, while the part not shaded appears relatively bright. As is apparent from FIG. 2, an annular part representing the bottle's mouth portion appears bright. A point, or a small area Ds in the annular area represents a defect in the mouth portion. For easier illustration, the optical image of FIG. 2 consists of the dark part and the bright part as described above; it should however be noted that, in practice, the optical image consists of parts with varying degrees of brightness.

The optical image as shown in FIG. 2 is scanned, so that picture element signals are produced successively. Each picture element signal is amplified by an amplifier 5, and is converted into a digital signal by an A/D converter 6. The digital signal is stored at the corresponding address in a data memory 7. The optical image is scanned line after line beginning with the top line.

A pulse generator 8 periodically a pulse to synchronize the reading of the picture element signal by the CCD camera 4 with the A/D conversion by the A/D converter 6. An address counter 9 counts the output pulses of the pulse generator, and the output of the counter 9 is used as the write address of the data memory 7.

Figure 3A:
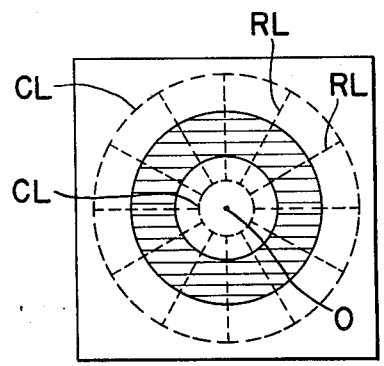
FIGS. 3A, 3B and 3C are explanatory diagrams schematically showing how the image of a bottle's mouth portion is imaginarily divided into regions.

The picture elements signals stored in the memory 7 are processed to determine whether the bottle has a defect or not, according to the following technical concept: As shown in FIG. 3A, the optical image of a bottle's mouth portion is divided by circles CL whose centers are the center O of the mouth portion and straight lines RL passing through the center O into a plurality of regions similar in configuration. The signals of the picture elements in each regions are accumulated to obtain the sum, and the sums or accumulation values for adjacent regions are subjected to comparison. When the ratio of the two sums is out of a predetermined range, it is determined that the bottle has a defect. The reason why this method enables detection of a defect in a bottle is that an abnormal region including a defect is much different in brightness from a normal region including no defect, e.g., the brightness of the abnormal region being much lower than that of the normal region.

Figure 4:
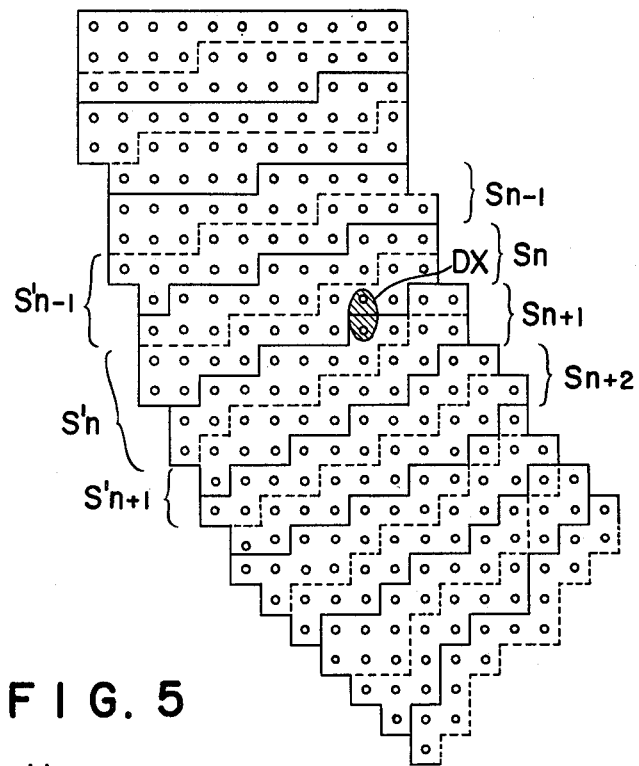
FIG. 4 is an explanatory diagram showing one example of the manner of dividing the picture elements forming the image of a bottle's mouth portion.

Since the photo-electric conversion elements are arranged in the form of a matrix, some of them may lie across the radial lines RL or the circumferences CL. Such elements are treated as belonging to one of the regions. In any case, the division of the image is effected in such a manner that the picture elements in all the regions are equal in number and the picture elements substantially at the equal distance from the center of the bottle's mouth portion are equal in number between the regions. FIG. 4 shows one example of the manner of dividing the picture elements. It should be noted that shown in FIG. 4 are only the picture elements which belong to the bright annular portion of the bottle's mouth. In this case, the area including the picture elements is divided into sixty-four (64 regions; however, FIG. 4 shows only ⅛ of them.

Processing the picture element signals according to the above-described technical concept is carried out as follows: When writing data in the memory 7 has been completed, reading data from the memory 7 is started. Thereupon, an address designating memory 10 designates the addresses of picture element signals to be read out, according to the outputs of the address counter 9. The addresses are designated in such a manner that, after the signals of all the picture elements in one region have been read out, reading of the signals of the picture elements in adjacent region is started. The data of the picture elements thus read are delivered to a discrimination circuit 11. When the discrimination circuit 11 determines that a bottle's mouth portion has a defect, i.e., the bottle should be rejected, the discrimination circuit 11 applies a defect signal DF to a rejecting device 12, so that the bottle is rejected from the conveyor line.

Figure 5:
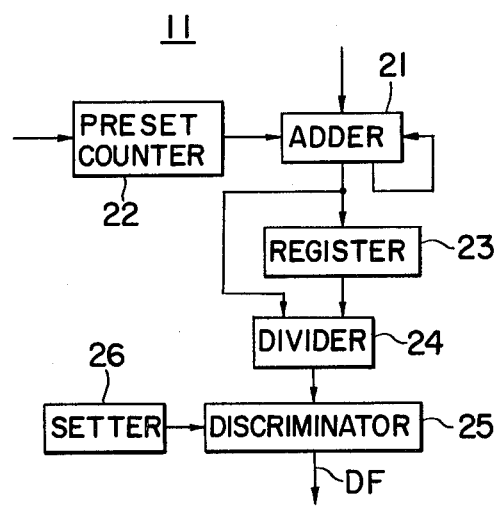
FIG. 5 is a block diagram showing one example of a discrimination circuit 11 in FIG. 1.

The discrimination circuit 11 has an internal construction as shown in FIG. 5. An adder 21 is used as an accumulator in which data read out of the memory 7 are added to the ouput thereof. The numbers of picture elements in the regions have been preset in a preset counter 22. Upon counting pulses from the pulse generator 8 up to the preset number, the preset counter 22 clears the adder 21 and causes the latter 21 to start the next accumulation. The output of the adder 21 is stored in a register 23 before cleared. In a divider 24, the output of the adder 21 is divided by the output of the register 23, i.e., by the sum resulting from the preceding accumulation, after the adder 21 has accumulated the data of the picture elements in the regions and before the adder is cleared. Thus, the ratio of the accumulation values of the data of the picture elements in the adjacent regions are obtained. A discriminator 25 operates to determine whether or not the ratio provided by the divider 24 is in a predetermined range. The upper limit value and the lower limit value of the predetermined range are preset by a setter 26, for instance 1.2 and 1/1.2. When the discriminator 25 determines that the ratio is out of the predetermined range, the discriminator 25 outputs the aforementioned defect signal DF.

The determination of presence or absence of a defect can be efficiently and accurately made detected in the above-described manner. However, where a defect (as indicated at DX in FIG. 4) extends over two regions $S_n$ and $S_{n+1}$ and occupies the substantially equal areas of the two regions, the result of comparison of the accumulation values for the adjacent regions $S_n$ and $S_{n+1}$ is hardly affected by the defect DX. On the other hand, the ratios of the accumulations of the regions $S_n$ and $S_{n+1}$ which include the halves of the defect, respectively, and regions $S_{n-1}$ and $S_{n-2}$ adjacent to the regions $S_n$ and $S_{n+1}$ are affected by the defect; however, the degree of the effect in this case is merely one half of what will result where the same defect is, in its entirety, in one region. Accordingly, discrimination based on the difference in accumulation values is difficult. In order to overcome this difficulty, the following method is employed: The picture elements are divided as indicated by the solid lines in FIG. 4. Accumulation values for the regions which are provided by this division are subjected to comparison. Furthermore, the picture elements are divided as indicated by the broken lines in FIG. 4. Accumulation values for the regions $S'_{n-1}$, $S'_n$, $S'_{n+1}$,... which are provided by the division are subjected to comparison. When, in any one of the comparisons described above, the ratio of accumulation values is determined to be out of a predetermined range, then it is determined that the bottle has a defect, i.e., it should be rejected. In order to practice the method, reading the data out of the memory 7 in the sequence as described above is carried out for the entire periphery of the bottle's mouth portion, and the address designating memory is caused to sequentially designate the addresses in the memory 7 so that, after the accumulation values for the regions indicated by the solid lines have been subjected to comparsion, the accumulation value of picture element data for each of the regions indicated by the broken lines is obtained. Then, comparison of the accumulation values of picture element data for the regions indicated by the broken lines is carried out for the entire periphery of the bottle's mouth portion. In this case, the effect of the defect DX appears clearly in the comparsion of the accumulation values for the regions indicated by the broken lines, and therefore detection of the defect is ensured.

Figure 3B:
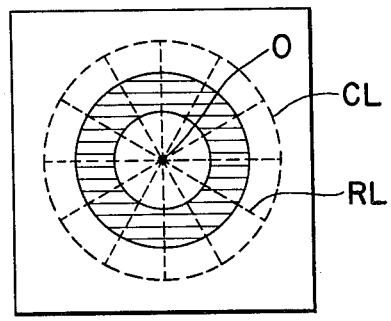
Figure 3C:
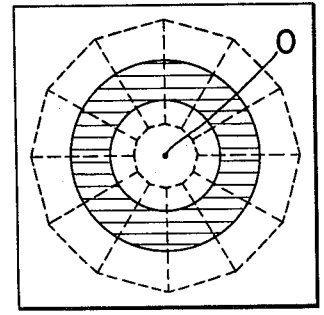

The manner of dividing the image is not restricted to that shown in FIG. 3A. Instead, the image may be divided into sector-shaped regions as shown in FIG. 3B or trapezoid regions as shown in FIG. 3C. Furthermore, the image may be divided into regions which are different in configuration from those described above. However, it is essential in any case that the dividing lines are so set that the accumulations values of picture element data for adjacent regions are substantially equal or in a substantially constant proportional relation, when an image of an object having no defect is formed.

In the above-described embodiment, the presence or absence of a defect is determined from the comparison of data for two regions which lies side by side; however, it may be determined from the comparison of data for two regions between which at least one region is disposed. Accordingly, the term "proximate" with reference to regions in the appended claims includes not only regions which lie side by side but also those between which at least one or a few regions are interposed.

In the above-described embodiment, the accumulation values of the data of all the picture elements in the regions are subjected to comparison; however, where the picture elements in the regions are not equal in number, a method may be employed in which an accumulation value is divided by the number of picture elements to obtain an average value, which is used for the comparison. Therefore, the term "result of accumulation" in the appended claims should be construed to cover the sum or accumulation value and the average value.

In the above-described embodiment, the ratio of the accumulation values or averages values for the regions is obtained, and then it is determined whether or not the ratio is out of the predetermined range; however, a method may be employed in which the difference between the accumulation values or average values is obtained and it is determined whether the difference is out of a predetermined range or not.

The term "predetermined range" is intended to mean not only one including the upper limit value and the lower limit value, but also one including one of the upper and lower limit values.

Figure 7A:
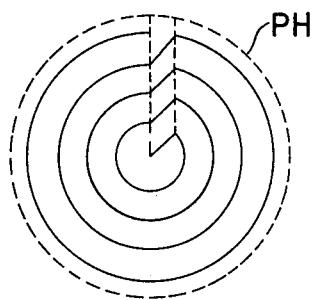
FIGS. 7A and 7B show examples of a spiral line which is used in determination of a sequence of reading data in the apparatus in FIG. 6.

FIG. 6 shows another embodiment of a defect detecting apparatus according to the invention. This apparatus is used to detect a defect in the bottom of a bottle. A light source $2'$ is provided under the bottom of a bottle 1, and a diffusion plate $2b'$ is interposed between the bottle's bottom and the light source $2'$. A camera 4 is disposed over the bottle 1. When light is applied to the bottom of the bottle 1 from the light source $2'$, the image of the bottom is formed on the light receiving surface of the camera 4. Signals representative of the brightness of each portion of the bottom are stored in a data memory 7, in a manner similar to that of the embodiment of FIG. 1. The apparatus has a first discrimination circuit 11 which is similar to that in FIG. 1 and a second discrimination circuit 31. In reading data out of the data memory 7, an address counter 9 and an address designating memory 10 designate data addresses in a manner similar to that of the apparatus shown in FIG. 1, and then makes addressing in such a manner that the picture element data are read out in the order in which segments or portions of an object corresponding to the picture elements are traversed by a substantially spiral imaginary line which is drawn on the object under inspection (described later in more detail). The spiral line may be as shown in FIG. 7A. As shown in FIG. 7A, the center of the spiral line is coincident with the center of the bottom of a bottle and the distance between the adjacent portions of the line is constant. In order to realize this, the addresses of data in the data memory 7 are stored in the address designating memory 10 in the sequence of reading, and as the address (input) supplied from the address counter 9 to the address designating memory 10 is increased, the content of the address, which constitutes the address of the data memory 7, is outputted. This technique has been disclosed in Japanese Patent Application Nos. 87510/1980 and 87511/1980.

Figure 8:
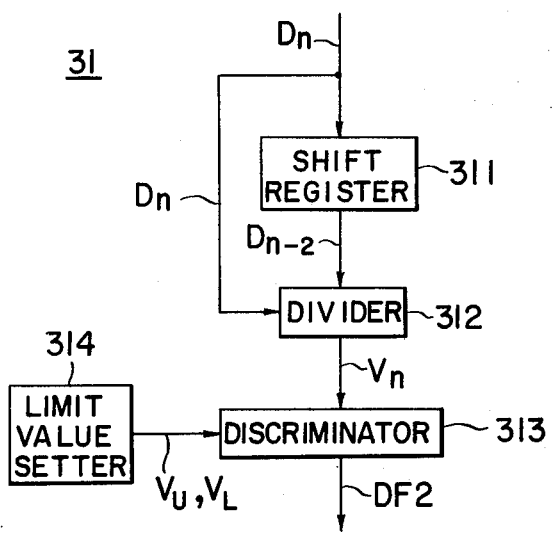
FIG. 8 is a block diagram of one example of a discrimination circuit (31) in FIG. 6.

The data read out in such a sequence are processed in the discrimination circuit 31, one example of which is shown in FIG. 8. Data $D_n$ read out of the memory 7 is inputted to a shift register 311. In the shift register 311, inputted data are stored and shifted successively. When two read cycles have passed since then, the shift register 311 produces the last-mentioned data as $D_{n-2}$. In a divider 312, the data $D_n$ which is being read out of the memory 7 is divided by the data $D_{n-2}$ from the shift register 311; that is, the divider 312 outputs the ratio of the two data, namely, $Vn$ ($=D_n/D_{n-2}$). Discriminator 313 determines whether or not the ratio $V_n$ is in a range having values $V_U$ (e.g., 1.5) and $V_L$ (e.g., 1/1.5) as the upper and lower limit values, which are set by a limit value setter 314. If the ratio $V_n$ is out of the range, the discriminator 313 outputs a signal DF2. The signal DF2 is applied to an input terminal of an AND gate 33, to the other input terminal of which an output of a gate control circuit 32 is applied. The output of the AND gate 33 is applied to an input terminal of an OR gate 34.

The gate control circuit 32 is responsive to the output of the address designating memory 10 to apply an "H" level signal to the AND gate 35 during the period when addressing for accumulation of picture element data for the regions is carried out, and to apply the "H" level signal to the AND gate 33 during the period when reading the picture element data along the spiral line is carried out. On the other hand, the output DF1 of the discrimination circuit 11 (corresponding to the signal DF in FIG. 1) is applied through the AND gate 35 to the other input terminal of the OR circuit 34. The output of the OR circuit 34 is employed as the defect signal DF, according to which the body under inspection is rejected from the inspection line.

Figure 9:
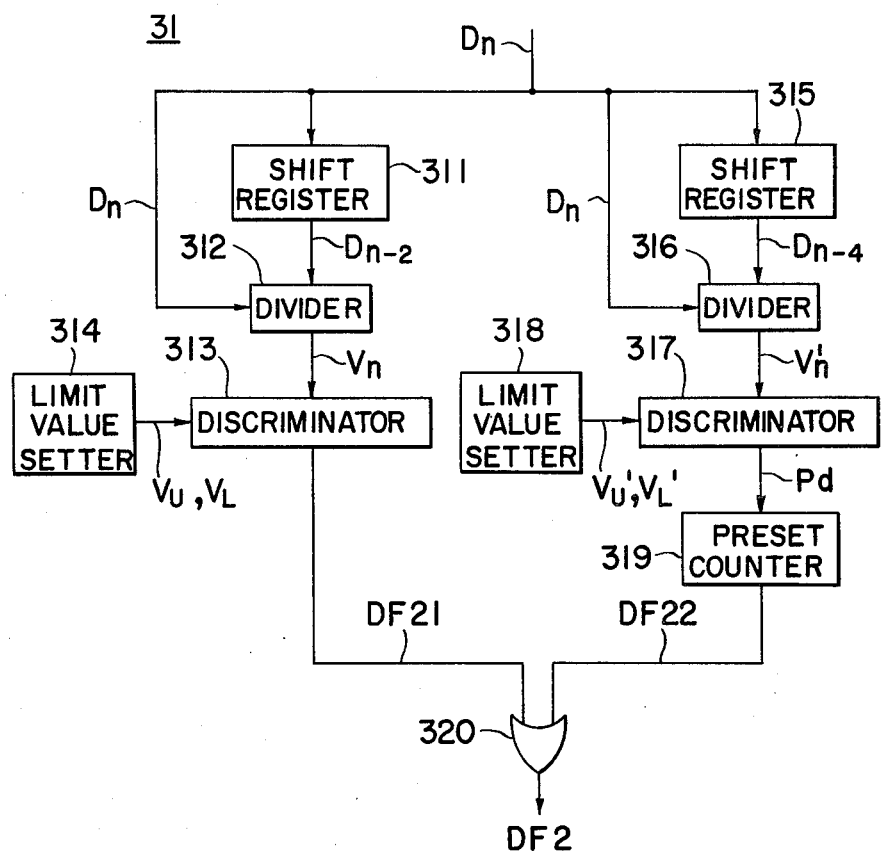
FIG. 9 is a block diagram of another example of the discrimination circuit (31) in FIG. 6.

Another example of the discrimination circuit 31 is shown in FIG. 9. The discrimination circuit 31 comprises a shift register 311, a divider 312, a discriminator 313 and a limit value setter 314 which are similar to those in FIG. 8. The output of the discriminator 313 is denoted by reference character DF21 instead of DF2 as will become apparent later. The discrimination circuit 31 further comprises a second shift register 315, in which the data read out of the memory 7 is stored and shifted. The data thus shifted is outputted as data $D_{n-4}$ after four read cycles. In a second divider 316, the data $D_n$ being read out of the memory 7 is divided by the data $D_{n-4}$ from the shift register 315; that is, a ratio $V_n'$ ($=D_n/D_{n-4}$) is provided. In a second discriminator, it is determined whether or not the ratio $V_n'$ is in a range having the upper limit value $V_U'$ (e.g. 1.1) and the lower limit value $V_L'$ (e.g. 1/1.1) which are set by a second limit value setter. The upper limit value $V_U'$ and the lower limit value $V_L'$ are selected to be closer to unity 11) than the values $V_U$ and $V_L$, as is apparent from the above description. A preset counter 319 counts the output pulse Pd of the discriminator 317, and it provides an output DF22. Either of the signals DF21 and DF22 passes through an OR circuit 320, becoming the signal DF2.

The provision of the shift register 315, divider 316, discriminator 317, limit value setter 318 and preset counter 319 enables detection of a defect whose brightness reduction is small but which spreads over a large area or a long distance.

Figure 10A:
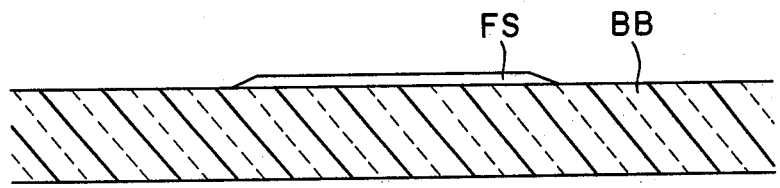
FIGS. 10A through 10C are diagrams illustrating the operation of the discrimination circuit in FIG. 9.
Figure 10B:
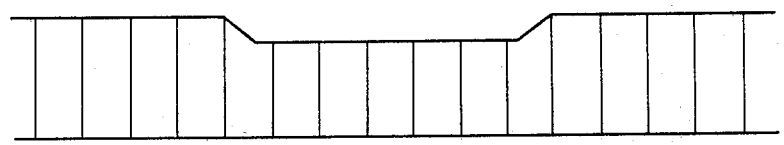
Figure 10C:

For instance when the relatively large area of the bottom BB of a bottle is slightly stained as indicated at FS in FIG. 10A, the data $D_n$ successively read out of the memory 7 are as shown in FIG. 10B. As is clear from FIG. 10B, the ratio of the two data is not out of the range ($V_L < V_n < V_U$). Accordingly, the discriminator 313 produces no signal DF21. However, some of the ratios which are obtained from two data (which are separated by other three data) are out of the range ($V_L' < V_n' < V_U'$). Therefore, the discriminator 317 produces an output pulse with the timing as shown in FIG. 10C. The output pulse is counted by the preset counter 319. When picture element data corresponding to the slightly stained portion is read successively four times, four pulses are provided at the beginning as well as at the end of the slightly stained portion. When the counting is effected up to the preset value (six (6)), the counter 319 outputs the signal DF22, which is applied to the OR circuit 320. Thus, the slight but extended stain for which the bottle should be rejected is detected. Where the number of output pulses from the discriminator 317 is smaller than the present value (six) (this phenomenon being caused for instance when the data variation is due to the presence of small stones within the glass), no signal DF22 is produced, and the bottle is not rejected.

The number of read cycles which occur during the time interval which elapses from the time instant that the shift register 315 receives data until the shift register 315 outputs it can be determined by selecting the number of stages or an output terminal of the register.

A plurality of circuits each comprising the shift register 315, the divider 316, the discriminator 317, the limit value setter 318 and the preset counter 319 as shown in FIG. 9 may be provided, with the circuits being made different from one another in the upper limit values ($V_U$, $V_U'$), the lower limit values ($V_L$, $V_L'$) and the preset value (the shift registers may or may not be different in the number of stage from one another), and with the outputs of these circuits being applied to an OR circuit similar to the OR circuit 320. In such a case, it is generally preferable to combine smaller counter preset value with larger upper limit values ($V_U$, $V_U'$). When these circuits as described are provided, then all the defects such as stains and foreign matters (for which bottles must be rejected) can be detected.

Instead of providing a plurality of combinations each comprising a shift register (311, 315) and a divider (312, 316), only one such combination may be provided with its output being used as inputs to all of a plurality of discriminators (313, 317).

In the above-described embodiment, it is determined whether or not the ratio of two signals is smaller than the upper limit value and larger than the lower limit value; however, a method may be employed in which the ratio is compared with only one of the upper and lower limit values.

Instead of the ratio of two signals, the difference between the two signals may be used in determining the variation of one signal with respect to another signal.

The range of signal variation and the counter preset value in accordance with which the presence or absence of a defect is detected may be changed depending on the positions (such as the center and the periphery of the bottom of a bottle) on an object under inspection.

In the above-described embodiment, the bottom of a bottle is scanned radially from the center of the bottom; however, it may be scanned radially starting with the periphery of the bottom.

Figure 7B:
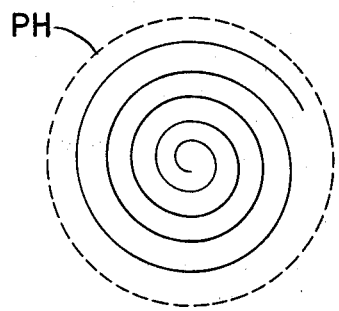

If the spiral line as shown in FIG. 7A is employed in the scanning operation, then the sequence of reading data out of the memory 7 can be readily determined. However, a spiral line as shown in FIG. 7B may alternatively be employed.

The sequence of reading data may be such that, whenever the spiral line traverses a segment or portion of an object under inspection, which corresponds to a picture element, the data of the picture element is read out, or alternatively, the data which has once been read by the scanning along the spiral line will not be read out again.

The position of the light source for applying light to an object under inspection and the arrangement of the television camera for receiving light from the object may be changed to suit the configuration and optical characteristic of the object. Instead of the CCD camera, a camera using solid-state image pickup elements such as BBD's may be employed as the image pickup camera, or an image orthicon type camera or a vidicon type camera may be employed.

In the above-described embodiment, the analog video signal is converted into the digital signal and is stored in the digital memory device; however, it may be stored, without being digitized, in an analog memory.

As is apparent from the above description, the invention provides a system wherein the data of the picture elements in each region of an object under inspection are accumulated, the accumulation values for near regions are subjected to comparison, and the presence or absence of a defect is determined from the comparison result. Accordingly, the presence or absence of a defect can be quickly and accurately determined without using a mechanism for spinning an object under inspection. In addition, inspection can be made uniformly through the entire portion (such as the mouth portion or the bottom of a bottle) of an object under inspection.

The above-described method in which the presence of absence of a defect is determined from the comparison of accumulation values for proximate regions (hereinafter referred to as "a region comparison method", when applicable) may be combined with other defect detecting methods, to improve the accuracy of defect detection.

If, as described with reference to FIG. 6, the region comparison method is employed in combination with the method (the latter method will be hereinafter referred to as "a spiral line method", when applicable) in the sequence of allowing the spiral line to cross portions in which the picture element signals are read out in the order in which the corresponding segments or portions are traversed by a spiral line, and the presence or absence of a defect is determined according to the result of comparison of the picture element signals which are closer in read sequence to each other, then the following merits can be obtained in the inspection of a bottle's bottom. The spiral line method is considerably effective in inspecting the central portion of a bottle's bottom; however, if the method is applied to the inspection of the peripheral portion of a bottle's bottom, then the determination may sometimes be erroneous because of the dark ring which appears owing to the meniscus. This is due to the fact that the dark ring is not always similar to and coaxial with the configuration of the bottle's bottom, and accordingly the spiral line sometimes crosses the dark ring at a relatively large angle. On the other hand, in the region comparison method, all that is necessary is to determine the boundaries of the region such that a dark ring or the like, accurate location, in advance, of which is difficult, lies in the regions. Thus, if the spiral line method is applied to the inspection of the central portion of a bottle's bottom and the region comparison method is applied to the inspection of the peripheral portion of the same, then a defect detecting method having the advantages of the two methods can be obtained.

What is claimed is:

1. A defect detecting method comprising the steps of:
   (a) receiving light from an object under inspection, to form an image thereof;
   (b) dividing said image into a plurality of picture elements;
   (c) storing signals of said picture elements in relation to the positions of the corresponding segments of said image;
   (d) imaginarily dividing said image into a plurality of regions;
   (e) accumulating said picture element signals for each region;
   (f) comparing the results of said accumulations of the regions proximate to each other; and
   (g) detecting a defect in said object in accordance with the result of said comparison.

2. A method as set forth in claim 1, in which said regions are formed by dividing said image with lines which are imaginarily drawn radially outwardly from the center of said image.

3. A method as set forth in claim 1, in which
   said picture element signals are accumulated for each of a first group of regions which are formed by dividing said image with a first group of lines which are imaginarily drawn radially outwardly from the center of said image, and the results of said accumulations of adjacent regions of said first group are compared to each other; and
   said picture element signals are accumulated for each of a second group of regions which are formed by dividing said image with a second group of lines which are imaginarily drawn radially outwardly from the center of said image, said second group of lines being interposed between said first group of lines, and the results of said accumulations of adjacent regions of said second group are compared to each other.

4. A defect detecting method comprising the steps of:
   (a) receiving light from an object under inspection, to form an image thereof;
   (b) dividing said image into a plurality of picture elements;
   (c) storing the signals of the picture elements in relation to the positions of the corresponding segments of said image;
   (d) reading the signals of said picture elements in the order in which the corresponding segments in the central area of said image are traversed by a substantially spiral line which is imaginarily drawn on said image;
   (e) detecting a defect in said object in accordance with the mutual relationship between the signal of one of the picture elements and the signal of another picture element read out a little before the reading of the signal of said one of the picture elements;
   (f) imaginarily dividing the peripheral part of said image into a plurality of regions;
   (g) accumulating the signals of said picture elements for each region;
   (h) comparing the results of said accumulations of regions proximate to each other; and
   (i) detecting a defect in said object in accordance with the result of said comparison.

5. A method as set forth in claim 4, wherein said object under inspection comprises a bottle and said method is used for detecting a defect in the bottom part of the bottle.

6. A method as set forth in claim 4, in which said regions are formed by dividing said image with lines which are imaginarily drawn radially outwardly from the center of said image.

7. A method as set forth in claim 4, in which
   said picture element signals are accumulated for each of a first group of regions which are formed by dividing said image with a first group of lines which are imaginarily drawn radially outwardly from the center of said image, and the results of said accumulations of adjacent regions of said first group are compared to each other; and
   said picture element signals are accumulated for each of a second group of regions which are formed by dividing said image with a second group of lines which are imaginarily drawn radially outwardly from the center of said image, said second group of lines being interposed between said first group of lines, and the results of said accumulations of adjacent regions of said second group are compared to each other.

8. A defect detecting apparatus comprising:
   (a) means for receiving light from an object under inspection, to form an image thereof;
   (b) means for storing signals of picture elements forming said image in relation to the positions of the corresponding segments of said image;
   (c) means for accumulating said picture element signals for each one of the regions which respectively form parts of said image;
   (d) means for comparing the results of said accumulations of regions proximate to each other; and
   (e) means for detecting a defect in said object under inspection in accordance with the result of said comparison.

9. An apparatus as set forth in claim 8, wherein said means (c) comprises means for accumulating said picture element signals for each one of the regions formed by dividing said image with lines which are imaginarily drawn radially outwardly from the center of said image.

10. An apparatus as set forth in claim 8, wherein said means (c) comprises means for accumulating said picture element signals for each of a first group of regions which are formed by dividing said image with a first group of lines imaginarily drawn radially outwardly from the center of said image and for each of a second group of regions which are formed by dividing said image with a second group of lines which are imaginarily drawn radially outwardly from the center of said image, said second group of lines being interposed between said first group; and said means (d) comprises means for comparing the results of said accumulations of adjacent regions of said first group and comparing the results of said accumulations of adjacent regions of said second group.

11. An apparatus as set forth in claim 8, further comprising:

(f) means for reading the signals of said picture elements in the order in which the corresponding segments are traversed by substantially spiral line which is imaginarily drawn on said image; and (g) means for detecting a defect in said object in accordance with the mutual relationship between the signal of one of the picture elements and the signal of another picture element read out a little before the reading of the signal of said one of the picture elements.

* * * * *